United States Patent
Ayirala et al.

(10) Patent No.: US 10,767,458 B2
(45) Date of Patent: Sep. 8, 2020

(54) CHARACTERIZATION OF CRUDE OIL-WATER INTERFACIAL FILM RIGIDITY TO ENHANCE OIL RECOVERY

(71) Applicant: Saudi Arabian Oil Company, Dhahran (SA)

(72) Inventors: Subhash Chandrabose Ayirala, Dhahran (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 240 days.

(21) Appl. No.: 15/912,065

(22) Filed: Mar. 5, 2018

(65) Prior Publication Data

US 2018/0291717 A1    Oct. 11, 2018

Related U.S. Application Data

(60) Provisional application No. 62/468,662, filed on Mar. 8, 2017.

(51) Int. Cl.

| | |
|---|---|
| *E21B 49/08* | (2006.01) |
| *C09K 8/68* | (2006.01) |
| *E21B 47/00* | (2012.01) |
| *E21B 21/00* | (2006.01) |
| *E21B 43/20* | (2006.01) |
| *G01N 33/18* | (2006.01) |
| *G01N 13/02* | (2006.01) |
| *G01N 11/10* | (2006.01) |
| *G01N 13/00* | (2006.01) |

(52) U.S. Cl.
CPC ............. *E21B 43/20* (2013.01); *E21B 49/08* (2013.01); *G01N 11/10* (2013.01); *G01N 13/00* (2013.01); *G01N 13/02* (2013.01); *G01N 33/1833* (2013.01)

(58) Field of Classification Search
CPC .......... C09K 8/685; C09K 8/887; C09K 8/04; C09K 8/487; C09K 8/508; C09K 8/90; E21B 21/003; E21B 43/26; E21B 43/263; E21B 43/30; E21B 43/305
See application file for complete search history.

(56) References Cited

U.S. PATENT DOCUMENTS 4,296,812 A    10/1981    Kalfoglou

OTHER PUBLICATIONS

Ayirala et al., "Water ion interactions at crude oil-water interface: A new fundamental understanding of SmartWater flood," SPE paper 183894 to be presented at the SPE Middle East Oil and Gas Show and Conference, Mar. 6-9, 2017, 17 pages.

Alves et al., "Influence of the salinity on the interfacial properties of a Brazilian crude oil-brine systems," Fuel (118), Feb. 15, 2014, 6 pages.

(Continued)

*Primary Examiner* — Zakiya W Bates
(74) *Attorney, Agent, or Firm* — Fish & Richardson P.C.

(57) ABSTRACT

Assessing a rigidity of an interface between a crude oil and a brine includes at least one of: assessing a compression energy for the interface between the crude oil and the brine; assessing a time at which an elastic modulus and a viscous modulus of the interface between the crude oil and the brine are equal; assessing a crumpling behavior or a crumpling ratio of a droplet of the crude oil in the brine; and assessing a coalescence time of droplets of the crude oil in the brine.

21 Claims, 14 Drawing Sheets

(56) References Cited

OTHER PUBLICATIONS

Lakatos and Lakatos-Szabo, "Effect of IOR/EOR chemicals on interfacial rheological properties of crude oil/water systems," SPE Paper 65391 presented at the 2001 SPE International Symposium on Oilfield Chemistry, Feb. 13-16, 2001, 10 pages.
Wasan et al., "Observations on the coalescence behavior of oil droplets and emulsion stability in enhanced oil recovery," Society of Petroleum Engineers of AIME, Dec. 1978, 9 pages.

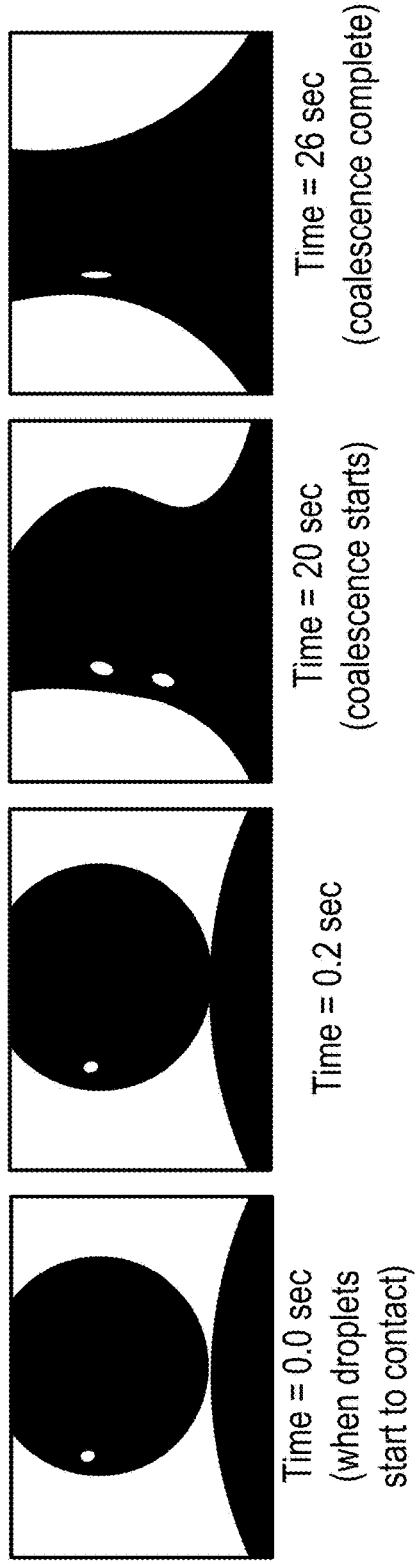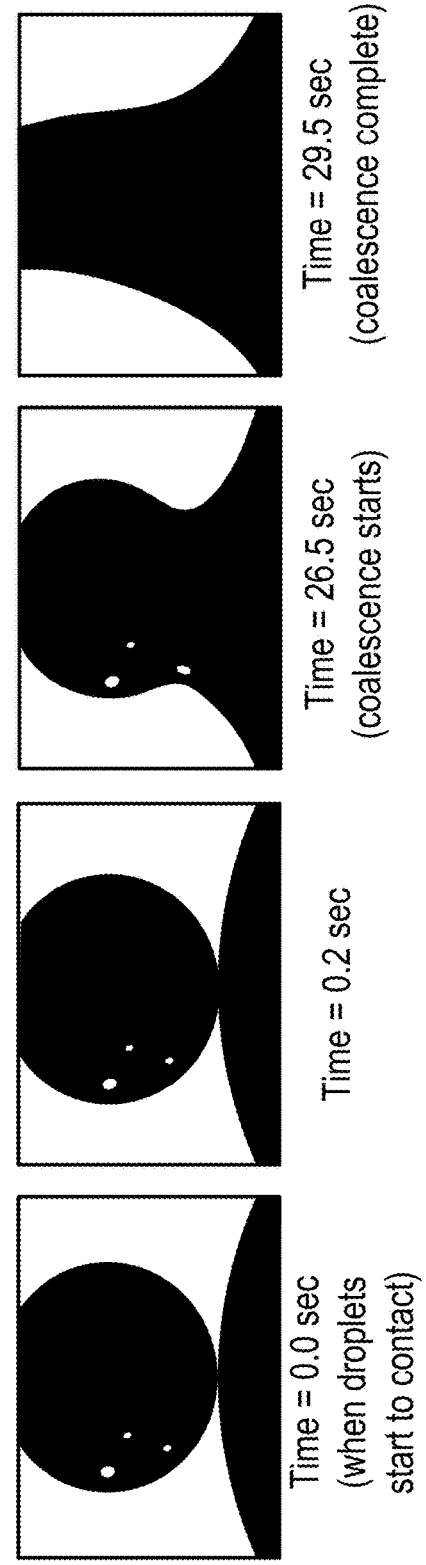
FIG. 15C
FIG. 15D

CHARACTERIZATION OF CRUDE OIL-WATER INTERFACIAL FILM RIGIDITY TO ENHANCE OIL RECOVERY

CROSS-REFERENCE TO RELATED APPLICATION

This application claims the benefit of U.S. Patent Application Ser. No. 62/468,662 entitled "CHARACTERIZATION OF CRUDE OIL-WATER INTERFACIAL FILM RIGIDITY TO ENHANCE OIL RECOVERY" and filed on Mar. 8, 2017, which is incorporated by reference herein in its entirety.

TECHNICAL FIELD

This disclosure relates to characterization of the rigidity of a crude oil-water interfacial film to enhance oil recovery.

BACKGROUND

Smart water flooding through tailoring of injection water salinity and ionic composition has been used to improve oil recovery in carbonate reservoirs. "Smart water" generally refers to water used for a water flooding process in which the ion composition of the water has been modified to improve wetting properties of the oil reservoir and enhance fluid flow and oil recovery in a porous medium during production. Surface and intermolecular forces, thin-film dynamics, and capillary and adhesion forces at rock-fluid interfaces impact crude oil liberation from pores. Stability and rigidity of oil-water interfaces influence the destabilization of interfacial films to promote coalescence between released oil droplets and contribute to recovery. As a result, oil recovery in smart water flooding is due at least in part to the combined effect of favorable interactions occurring at oil-brine interfaces and oil-brine-rock interfaces in formations.

SUMMARY

In a first general aspect, assessing a rigidity of an interface between a crude oil and a brine includes at least one of: assessing a compression energy for the interface between the crude oil and the brine; assessing a time at which an elastic modulus and a viscous modulus of the interface between the crude oil and the brine are equal; assessing a crumpling behavior or a crumpling ratio of a droplet of the crude oil in the brine; and assessing a coalescence time of droplets of the crude oil in the brine.

In a second general aspect, selecting a composition of an injection fluid for an enhanced oil recovery process includes assessing a rigidity of an interface between a crude oil and a brine, and selecting the composition of the injection fluid. Selecting the composition of the injection fluid includes altering a composition of the brine to increase or decrease a concentration of one or more ions in the brine to yield the injection fluid, such that the crude oil-injection fluid interfacial film rigidity is less than the crude oil-brine interfacial film rigidity.

In some implementations, the second general aspect includes at least one of: assessing a compression energy for the interface between the crude oil and the brine; assessing a time at which an elastic modulus and a viscous modulus of the interface between the crude oil and the brine are equal; assessing a crumpling behavior or a crumpling ratio of a droplet of the crude oil in the brine; and assessing a coalescence time of droplets of the crude oil in the brine.

Implementations of the first and second general aspects may include one or more of the following features.

In some embodiments, assessing a compression energy for the interface between the crude oil and the brine includes assessing interfacial pressure versus area isotherms for the interface between the crude oil and the brine, and integrating the interfacial pressure over the surface area change to yield the compression energy. Assessing the interfacial pressure versus area isotherms for the interface between the crude oil and the brine may be achieved with a Langmuir trough. Assessing the rigidity of the interface between the crude oil and the brine may include assessing the compression energy for the interface between the crude oil and the brine, and selecting a composition of an injection fluid for the reservoir from which the crude oil was obtained by increasing or decreasing a concentration of at least one ion in the brine to decrease the rigidity of the interface between the crude oil and the brine.

In some embodiments, assessing a time at which an elastic modulus and a viscous modulus of the interface between the crude oil and the brine are equal includes assessing elastic moduli and viscous moduli of the interface between the crude oil and the brine as a function of time, and identifying a time at which the elastic modulus is equal to the viscous modulus. In certain embodiments, the first or second general aspect includes assessing a dynamic interfacial viscosity using the elastic moduli and the viscous moduli. Assessing the elastic moduli and viscous moduli of the interface between the crude oil and the brine as a function of time may be achieved with an interfacial shear rheometer. Assessing the rigidity of the interface between the crude oil and the brine may include assessing the time at which the elastic modulus and the viscous modulus of the interface between the crude oil and the brine are equal, and selecting a composition of an injection fluid for the reservoir from which the crude oil was obtained by increasing or decreasing a concentration of at least one ion in the brine to decrease the rigidity of the interface between the crude oil and the brine.

In some embodiments, assessing a crumpling ratio of a droplet of the crude oil in the brine includes assessing an initial size of a droplet of the crude oil in the brine before initiating a contraction of the droplet of the crude oil, and assessing a size of the droplet of the crude oil in the brine at the time at which crumpling begins. The crumpling ratio is a projected area of the oil droplet just before it crumples divided by the projected area of the initial droplet.

In some embodiments, the brine includes ions of at least one of sodium, calcium, magnesium, chloride, bicarbonate, and sulfate. In certain embodiments, the brine is substantially free of sulfate. Assessing the rigidity of the interface between the crude oil and the brine may include assessing the crumpling behavior or the crumpling ratio of the droplet of the crude oil in the brine, and selecting a composition of an injection fluid for the reservoir from which the crude oil was obtained by increasing or decreasing a concentration of at least one ion in the brine to decrease the rigidity of the interface between the crude oil and the brine.

In some embodiments, assessing the rigidity of the interface between the crude oil and the brine includes assessing a coalescence time of droplets of the crude oil in the brine, and selecting a composition of an injection fluid for the reservoir from which the crude oil was obtained by increasing or decreasing a concentration of at least one ion in the brine to decrease the rigidity of the interface between the crude oil and the brine.

In some embodiments, the first or second general aspect includes obtaining a sample of the crude oil from a reservoir before assessing the rigidity of the interface between the crude oil and the brine, selecting a composition of an injection fluid for the reservoir from which the crude oil was obtained by increasing or decreasing a concentration of at least one ion in the brine to decrease the rigidity of the interface between the crude oil and the brine, and injecting the injection fluid into the reservoir.

In some embodiments, the first and second general aspects include obtaining a sample of the crude oil from a reservoir before assessing the rigidity of the interface between the crude oil and the brine. In certain embodiments, the first and second general aspects include injecting the injection fluid into the reservoir.

In some embodiments, a concentration of at least one of sodium ions, calcium ions, magnesium ions, chloride ions, bicarbonate ions, or sulfate ions may be increased in the brine to decrease the rigidity of the interface between the crude oil and the brine. In certain embodiments, a concentration of sulfate ions in the brine may be decreased to decrease the rigidity of the interface between the crude oil and the brine.

Embodiments described herein provide a robust measurement work flow using different interfacial techniques to quantify oil-water interfacial film rigidity, which is used to enhance EOR processes by improving the coalescence of crude oil droplets, thereby enabling oil phase connectivity, quick oil bank formation and faster oil recovery.

The details of one or more implementations of the subject matter described in this specification are set forth in the accompanying drawings and the following description. Other features, aspects, and advantages of the subject matter will become apparent from the description, the drawings, and the claims.

BRIEF DESCRIPTION OF THE DRAWINGS

FIGS. 15A-15E show dynamic coalescence behavior of crude oil droplets in various brines.

DETAILED DESCRIPTION

Crude oil-water interfacial film rigidity influences the coalescence behavior of released oil droplets in enhanced oil recovery (EOR) technologies including smart water flooding and chemical flooding processes with surfactants. Interfacial parameters such as interface pressures, interface compression energies, interface viscosities, transition time of an interfacial film from a viscous regime to an elastic regime, crumpling ratio of crude oil droplets, and coalescence times can be used to adjust the type and concentration of ions at the crude oil-water interface to enhance the coalescence of oil droplets, oil phase connectivity and promote quick formation of an oil bank in a reservoir for faster oil recovery and improved oil cut in production.

Figure 1A:
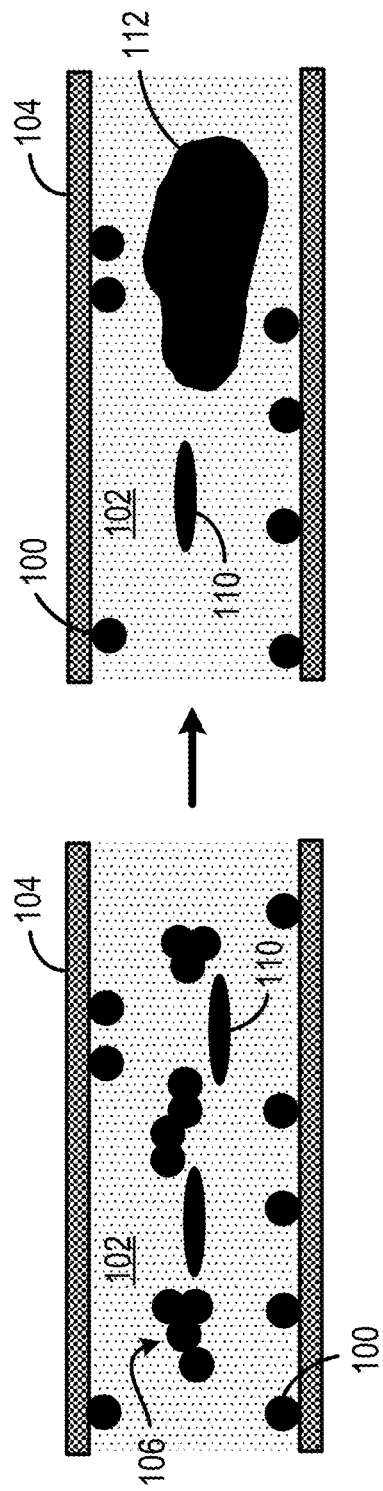
FIG. 1A depicts coalescence of oil droplets to form an oil bank in a water flooding process.
Figure 1B:
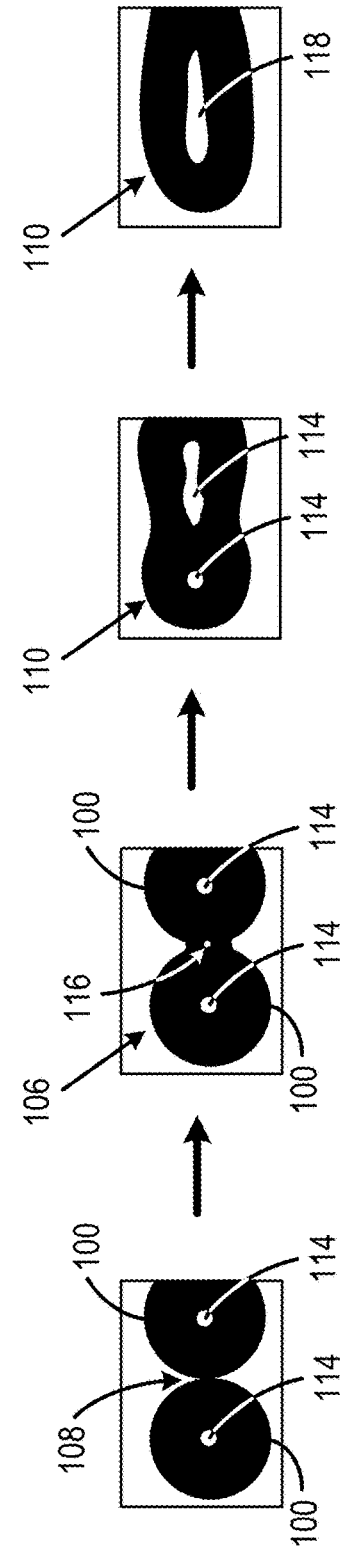
FIG. 1B shows an enlarged view of the coalescence of oil droplets in FIG. 1A.

FIG. 1A depicts a mixture of oil droplets 100 and water 102 flowing through conduit 104 during a water flooding process. The coalescence of oil droplets 100 to form aggregates 106 is governed at least in part by the rigidity of the crude oil-water interfacial film. Water film 108 confined between oil droplets 100 can thin and drain, rupturing the oil-water interfacial film and initiating coalescence to form coalesced droplet 110. Over time, coalesced droplets 110 merge to form oil bank 112. FIG. 1B depicts an enlarged view of the progression of coalescence of oil droplets 100 to yield coalesced droplet 110. As depicted in FIG. 1B, oil droplet 100 may have water inclusion 114. As oil droplets 100 form aggregate 106, water film 108 can form an additional water inclusion 116 between oil droplets 100. As coalesced droplet 110 forms, additional water inclusion 116 may merge with water inclusions 114 in oil droplets 100 to yield combined water inclusion 118. Coalesced droplets 110 merge to form oil bank 112, as depicted in FIG. 1A.

As understood with respect to FIGS. 1A and 1B, the strength or the rigidity of the interfacial layer can be a factor in the difficulty of thin film rupture, with the less rigid films being favored for the coalescence of the droplets and formation of an oil bank. The quick formation of an oil bank by the coalescence of oil droplets and subsequent oil phase connectivity can promote faster oil recovery with increased oil cut in the production.

Figure 2:
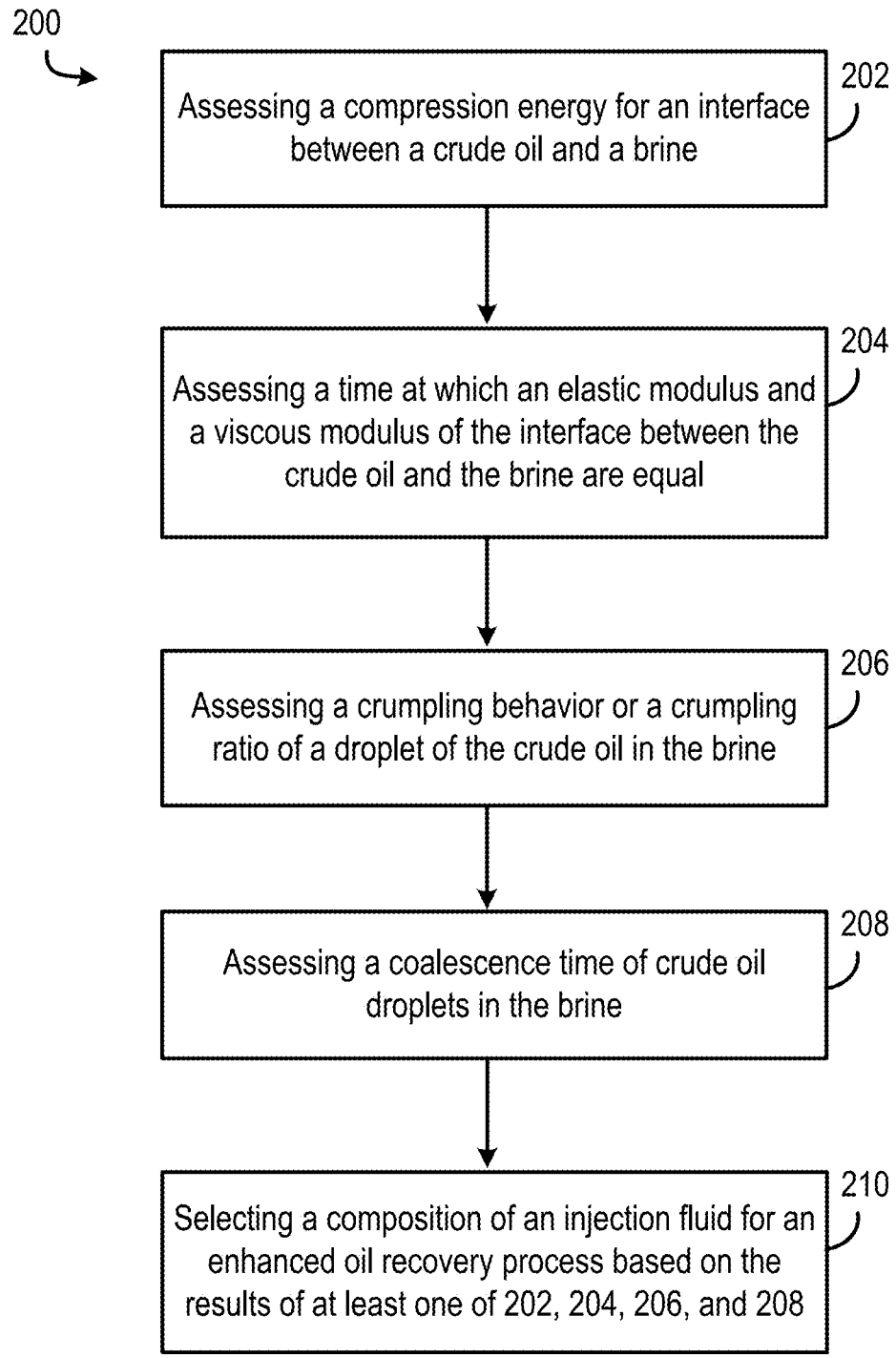
FIG. 2 is a flow chart showing a process for assessing a rigidity of an interface between a crude oil and a brine, and selecting a composition of an injection fluid to enhance oil recovery in an enhanced oil recovery (EOR) process based on the assessed rigidity of the interface between the crude oil and the brine.

Referring to FIG. 2, process 200 includes assessing a rigidity of an interface between a crude oil and a brine, and selecting a composition of an injection fluid to enhance oil recovery in an EOR process based on the assessed rigidity of the interface between the crude oil and the brine. As used here, "brine" generally refers to an aqueous composition including one or more salts dissolved to yield ions such as sodium, calcium, magnesium, chloride, bicarbonate, and sulfate. A brine may be substantially free or contain minimally adequate amounts of one or more ions, such as sulfate. The brine may also include one or more additives, such as surfactants, polymers, and nanoparticles. In some embodiments, a total dissolved solids (TDS) in a brine is in a range of about 5,000 to about 57,000 parts per million (ppm) by weight.

In 202, a compression energy for an interface between a crude oil and a brine is assessed. Assessing the compression energy includes assessing interface pressure versus area isotherms for an interface between the crude oil and the brine. The interface pressure versus area isotherms may be assessed using a Langmuir trough. A greater interfacial pressure at the given area typically corresponds to a more rigid interface, while a smaller interfacial pressure at the given area typically corresponds to a less rigid interface. Integration of the interfacial pressure over the surface area change yields the compression energy. A larger compression energy for the crude oil-brine interfacial film typically corresponds to a stronger interfacial film rigidity, while a smaller compression energy typically corresponds to a weaker interfacial film rigidity.

In 204, the time at which an elastic modulus (G') and a viscous modulus (G") of the crude oil-water interface are equal is assessed. Assessing the time at which the elastic modulus and the viscous modulus are equal includes assessing the elastic moduli and viscous moduli as a function of time. The elastic moduli and viscous moduli of the crude oil-brine interface may be assessed using an interfacial shear rheometer. A dynamic interface viscosity is assessed using the measured viscous and elastic moduli. A larger dynamic interface viscosity typically corresponds to a stronger interfacial film rigidity, while a smaller dynamic interface viscosity typically corresponds to a weaker interfacial film rigidity. From the measured data, a time at which the interfacial film transitions from viscous-dominant (G">G') to elastic-dominant (G'>G") is assessed. In other words, the transition time is the time it takes for G' to equal G". A shorter transition time is typically indicative of a more stable, rigid film, at least in part because an elastic-dominant interface is more difficult to rupture.

In 206, a crumpling ratio of a droplet of the crude oil in the brine is assessed. The crumpling ratio is the ratio of the projected area of oil droplet just before it crumples in the brine to the projected area of initial droplet. Assessing the crumpling ratio of the crude oil includes assessing the crumpling behavior of a droplet of the crude oil when it contracts after aging in the brine. The crumpling behavior of the crude oil droplet when it contracts after aging in the brine may be assessed using a tensiometer. An initial size of the crude oil droplet (at the starting point of contraction) is assessed, and a size of droplet at the starting point of crumpling is assessed. A larger crude oil droplet at the start of crumpling typically corresponds to a more rigid interfacial film, while a smaller crude oil droplet at the start of crumpling typically corresponds to a less rigid interfacial film. The crumpling ratio is a quantitative measure of interfacial film rigidity. A larger crumpling ratio is typically indicative of a more rigid interface, while a smaller crumpling ratio is typically indicative of a less rigid interface.

In 208, a coalescence time of crude oil droplets in the brine is assessed. A longer coalescence time typically corresponds to a more rigid interfacial film, while a shorter coalescence time typically corresponds to a less rigid interfacial film.

In 210, a composition of an injection fluid for an EOR process is selected based on the crude oil-brine interfacial film rigidity assessed in at least one of 202, 204, 206, and 208. Selecting the composition of the injection fluid may include altering a composition of the brine to increase or decrease a concentration of one or more ions in the brine to yield the injection fluid, such that the crude oil-injection fluid interfacial film rigidity is less than the crude oil-brine interfacial film rigidity. Selecting a composition of an injection fluid based on the crude oil-brine interfacial film rigidity assessed in at least one of 202, 204, 206, and 208 may synergistically combine the beneficial effects of water ion interactions at crude oil-brine interfaces with those at rock-fluid interfaces (such as rock-crude oil interfaces or rock-brine interfaces). This synergy may promote faster oil recovery without substantially compromising ultimate recovery, which may be primarily governed by interactions at the rock-fluid interface.

Some embodiments of process 200 include injecting the injection fluid having the selected composition into the reservoir from which the crude oil was obtained.

As described with respect to process 200, film rigidity of an interfacial film between a crude oil and a brine is quantified by compression energy of the interfacial layer (Langmuir trough), G'=G" time (shear rheology), dynamic interface viscosities (shear rheology), and crumpling ratio. In some embodiments, one or more operations in process 200 may be omitted. In some embodiments, for example, process 200 includes one of 202, 204, 206, or 208, with or without 210. In other embodiments, process 200 includes 210 and at least two of 202, 204, 206, and 208. In some embodiments, process 200 may include one or more additional operations not shown in FIG. 2. Operations in process 200 may be initiated in any order. In certain embodiments, one or more operations in process 200 occur at the same time (that is, overlap in time).

Example

Experimental investigation was carried out to understand the effects of different water ions at crude oil-water interface, using instruments such as a Langmuir trough, interfacial shear rheometer, attension tensiometer, and coalescence time measurement apparatus. These instruments have resolution limits down to the molecular scale, and the associated techniques can quantify dynamic variations in the properties of the crude oil-water interface besides measuring the coalescence time between oil droplets with changing aqueous phase salinities and individual ion concentrations. The crude oil from a typical Saudi Arabian reservoir and four different brines with varying salinities and individual ion concentrations were used. Interface pressures, compression energy, interfacial viscous and elastic moduli, oil droplet crumpling ratio, and coalescence time between crude oil droplets were measured.

Interfacial pressures gradually increased with compression of surface area for all the brines and deionized (DI) water. The compression energy (integration of interfacial pressure over the surface area change), indicating rigid interfaces, is the greatest for DI water, followed by a low-salinity brine containing sulfate ions. The transition times of the interfacial layer to from a viscous-dominant to an elastic-dominant structure was found to be much shorter for brines enriched with sulfates, once again confirming the rigidity of interface. The crumpling ratios (oil drop wrinkles when contracted) were also greater for DI water and the sulfates-only brine, confirming the elastic rigid skin at the interface. The coalescence time between oil droplets were the shortest in brines containing a sufficient amount of calcium, magnesium and sodium ions, and the longest in DI water and sulfate-rich brine. These results showed correlation of coalescence times with the rigidity of oil-water interface, as interpreted from different measurement techniques, and provided comprehensive characterization of the crude oil-water interface with respect to microscopic scale water ion interactions and mechanisms responsible for coalescence between crude oil droplets in Smart water flood. The results also indicated the significance of both salinity and certain ions, such as calcium and magnesium in the Smart water, to enhance the coalescence between released crude oil droplets, oil phase connectivity and quickly form an oil bank in the reservoir for faster oil recovery.

The experiments described in this section were designed to:

(1) determine the compression rheology of crude oil-water interface by measuring interface pressure versus average molecular area isotherms, (2) study the viscoelastic (viscous and elastic moduli) behavior of interfacial film at crude oil-water interface as function of salinity and individual ion compositions, (3) quantify the presence of rigid (elastic) "skin" at the crude oil-water interface by determining the "crumpling ratio" of an aged oil droplet in different brines, and (4) correlate different microscopic scale interactions of water ions measured at the crude oil-water interface with crude oil droplet coalescence times and provide an understanding of underlying interfacial sciences that govern oil recovery from a Smart water flood.

Materials

Brines.

Different salts such as magnesium chloride, calcium chloride dihydrate, sodium sulfate anhydrous, sodium chloride, and sodium bicarbonate were used to prepare different synthetic brine solutions. These salt compounds were obtained from Thermo Fisher Scientific and were all of certified American Chemical Society (ACS) grade. The Thermo Fisher Scientific NanoPure™ system was used to produce deionized (DI) water having a resistivity of 18.2 megaohm-centimeters (MΩ·cm) at 25 degrees Celsius (° C.). Several synthetic brines with varying monovalent and divalent ions were prepared to study the effects of both salinity and individual water ions on microscopic scale interactions occurring at crude oil-water interface. The compositions of different synthetic brines used in experiments are shown in Table 1. Four synthetic brine samples (Brines 1-4) were prepared to study both seawater dilution and individual water ion effects. Brines 1-4 represent typical Gulf seawater; seawater enriched with calcium, magnesium, and sulfates; seawater diluted 10-fold; and seawater diluted 10-fold and enriched with sulfates, respectively. DI water was also used as a control to provide baseline comparisons.

TABLE 1

Composition of Brines 1-4

| Ion | Symbol | Brine 1 (ppm) | Brine 2 (ppm) | Brine 3 (ppm) | Brine 4 (ppm) |
|---|---|---|---|---|---|
| Sodium | $Na^+$ | 18,300 | 2,053 | 1,824 | 1,865 |
| Calcium | $Ca^{2+}$ | 650 | 650 | 65 | 0 |
| Magnesium | $Mg^{2+}$ | 2,110 | 2,110 | 211 | 0 |
| Sulfate | $SO_4^{2-}$ | 4,290 | 4,290 | 429 | 3,896 |
| Chloride | $Cl^-$ | 32,200 | 7,304 | 3,220 | 0 |
| Bicarbonate | $HCO_3^-$ | 120 | 0 | 12 | 0 |
| TDS | | 57,670 | 16,407 | 5,761 | 5,761 |

Crude Oil.

Figure 3:
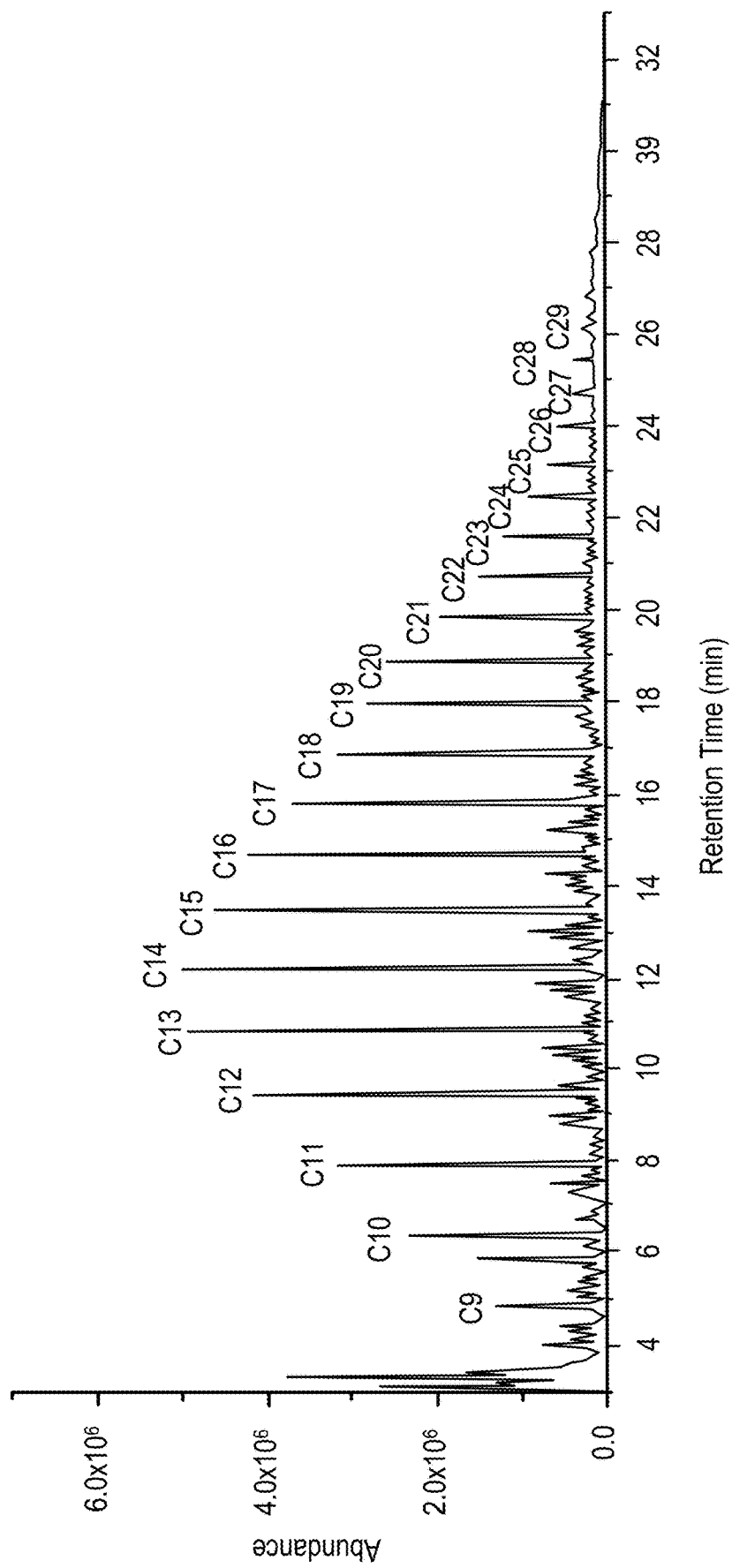
FIG. 3 is a total ion chromatogram of a crude oil sample.

Stock tank crude oil collected from the gas-oil separation plant (GOSP) of a Saudi Arabian reservoir was used. The impurities such as solids and water from the crude oil sample were removed using centrifuge methods. The oil was a light crude oil (34 degrees American Petroleum Institute gravity) and had a viscosity of about 6.0 centipoise (cP). The total ion chromatogram (TIC) of the crude oil sample is shown in FIG. 3. As can be seen, the dominant components on the TIC correspond to linear saturated alkanes ($n$-$C_mH_{2m+2}$) with carbon numbers (m) ranging from $C_9$ to $C_{30}$. The asphaltene content was in the range of 2.4 to 2.5 weight percent (wt %). The total acid number (TAN) and the total base number (TBN) were determined to be 0.0561 milligrams of potassium hydroxide per gram of oil (mg KOH/g) and 0.7059 mg KOH/g, respectively.

Methods

Langmuir Trough.

The compressional behavior of crude oil interfacial films at the dectol-water (brines/DI) interface was characterized by interfacial pressure-area (π-A) isotherm obtained using Langmuir trough. The experiments were conducted using a computer-controlled KSV trough (Biolin Scientific, Espoo, Finland) which has a total trough area of 170 square centimeters ($cm^2$). A paper Wilhelmy plate sensor (Biolin Scientific; product identification, KN 0005) was used to detect the interfacial pressure (π) which represents the change in the interfacial tension (IFT) due to the presence of interfacial material relative to the clean interface ($IFT_o$), as given by:

$$\pi = IFT_o - IFT \qquad \text{Eq. (1)}$$

Prior to each measurement, the trough was carefully cleaned sequentially with toluene, acetone, and Milli-Q water. The lower part of the trough was filled with 120 milliliters (mL) of Milli-Q water as the subphase. The trough was considered clean when the pressure isotherm at the air-water interface has a pressure reading less than 0.1 millinewton per meter (mN/m) with the water phase being compressed from 170 $cm^2$ to 1 $cm^2$. The barriers were then fully expanded and the balance was zeroed at clean air-water interface. 100 mL of dectol (volume of decane:toluene=50:50) was then added to the top of DI water as the top phase, followed by the injection of 23 microliters (µL) of 20 wt % crude oil in toluene solution into the top dectol phase using a Hamilton gastight syringe. After equilibrating the film for 1 hour, the system was compressed at 10 millimeters per minute (mm/min) to obtain the pressure-area (π-A) isotherms. The measurements were then repeated using the same steps by replacing DI water with Brines 1-4.

Shear Rheology.

The viscoelastic properties (elastic-G' and viscous-G") and the dynamic (complex) viscosities of the crude oil-brine interfacial layers were determined using an AR-G2 stress-controlled rheometer (TA Instruments, New Castle, Del., USA) equipped with a double-wall ring (DWR) geometry which is made of platinum-iridium. The radius of the DWR was 35 millimeters (mm), and its square-edged cross section helped to pin it at the oil-water interface. The ring was flamed before each experiment to remove all the organic contaminants.

Pipetted first into the sample holder was 19.2 mL of one of Brines 1-4 as the bottom phase or sub-phase. After positioning the ring at the air-aqueous solution interface, 15 mL of crude oil was slowly pipetted onto the top of the brine. Finally, a Teflon cap was placed over the sample to prevent solvent evaporation. To study the effect of aging on viscoelastic properties of interfacial layers, time sweeps were conducted at an angular frequency of 0.5 hertz (Hz) for 5 hours.

Crumpling Ratio.

To quantitatively analyze the skin formation at the surface of crude oil droplet in aqueous phase, the crumpling ratio was determined through a volume contraction process by means of a tensiometer (Theta Optional Tensiometer, Attension, Biolin Scientific, Finland). In this study, a pendant drop of diluted crude oil (0.5 wt % of crude oil in dectol (decane:toluene=1:1) was generated through a gastight syringe (Hamilton Co., USA) with an 18-gauge needle, and immersed in Brines 1-4/DI water. The initial volume of the drop was kept constant at 30 µL, and the drop was aged in the aqueous solution for 30 minutes. After aging, the volume of the diluted crude oil droplet was steadily decreased by extending the syringe. The whole process starting from the contracting until the visible appearance of wrinkles around the droplet at sufficient contraction was recorded with the camera at 1 frame per second (fps) framing rate. The crumpling ratio was quantified by dividing the projected area of the droplet immediately prior to wrinkles formation by the projected area of the droplet immediately prior to the volume contraction.

Coalescence Time.

A 40-watt speaker with a frequency range of 90-15,000 Hz was used as the power driver. The movement of the top crude oil droplet was controlled by the drum of the speaker through a glass capillary tube (inner diameter of 0.89 mm and outer diameter of 1.33 mm). The crude oil droplet of controllable size was generated at the end of the capillary tube by a Gilmont micro-syringe. A 40× lens and a charge-coupled device (CCD) camera were used to assist precise positioning (alignment) of the top oil drop in relation to the bottom oil drop held on a Teflon disk fixed on a bimorph force sensor and viewing the contacting process. An amplifier interfaced with a computer was used as a power source to drive the speaker and hence the top oil drop, while the charge signal generated from the bimorph as a result of deformation in response to an applied external force from the top oil drop was measured using a charge amplifier, also interfaced to the computer. A Z4D-F04A (Omron, Japan) micro-displacement sensor was mounted 4 mm below the drum of the speaker to detect the actual displacement of the drum and hence the capillary tube driving the top oil drop.

The amplitude and duration of the displacement were set at 0.2 micrometer ($\mu$m) and 0.1 milliseconds (ms) resolution, respectively. A 12-bit DAS-16F (Omega) DA/AD board was installed on a desktop computer for data acquisition. A custom-designed software allowed instructions to be sent to the controller and signals to be received from the sensor in real time. A timer on the DA/AD board was programmed to generate 10,000 Hz pulses to ensure a precision of 0.1 ms. A three-dimensional micro-translation station was used to position and align the samples held in a glass cell equipped with a water jacket. The experimental procedure followed for measuring the oil droplets coalescence time in different brines/DI water is described below.

1) A top crude oil droplet was generated through the glass capillary tube which was connected to a micro-syringe through plastic tubing fastened underneath the speaker. The glass capillary tube was initially filled with DI water, and then with the crude oil sample by sucking the crude oil to about half of the tubing length.

2) A steel container with flat windows containing Brines 1-4/DI water and a Teflon holder was placed on a triaxial translation stage under the speaker in such a way that a half of the capillary tube was immersed in the brine. The oil drop on the capillary tube was made in contact with the Teflon holder, which generated a semicircular crude oil drop of 0.78 mm height on the Teflon holder. The capillary tube was then lifted up to leave space for the generation of the top crude oil droplet (diameter of 3.18 mm).

3) After aging for 30 minutes in Brines 1-4, the top droplet was brought to 0.15 mm above the bottom drop and the measurement started. The speaker controlled by the software brought the top drop towards the bottom drop at an approaching velocity of 0.3 millimeters per second (mm/s). The overlap of the two droplets was controlled to be 0.15 mm after approaching for 1 second. The top droplet was then held still, while the CCD camera was recording the process of the drop approaching and 2-minute holding. The coalescence time was calculated as the time from initial contact (when the distance between the two droplets is 0) to the time of coalescence (when the two droplets combine into one droplet), by analyzing the videos on the play back mode.

4) After each experiment, the capillary tube and the contained crude oil sample was replaced to avoid the irreversible change of crude oil-brines interfaces. The brine solution was disposed and the container was cleaned by toluene, acetone, and DI water sequentially. The cleaned container was then blown dry with compressed air for the next experiment.

5) For an accurate measurement, the size of both the top and bottom drops was accurately controlled, and the capillary tube was replaced for each experiment. Furthermore, the top and bottom drops were aligned accurately in both x and y directions with the help of the lens and microscope, respectively.

Langmuir Trough.

The crude oil-Brines 1-4/DI water interface was formed by the diffusing of the concentrated crude oil through the dectol phase to the dectol-aqueous interface. The effect of the brine composition on the interfacial pressure was studied by recording the oil-water interfacial pressure ($\pi$) as the oil-Brines 1-4/DI water interface was compressed. The interfacial pressure versus molecular area isotherms obtained with Brines 1-3/DI water are summarized in FIG. 4.

Figure 4:
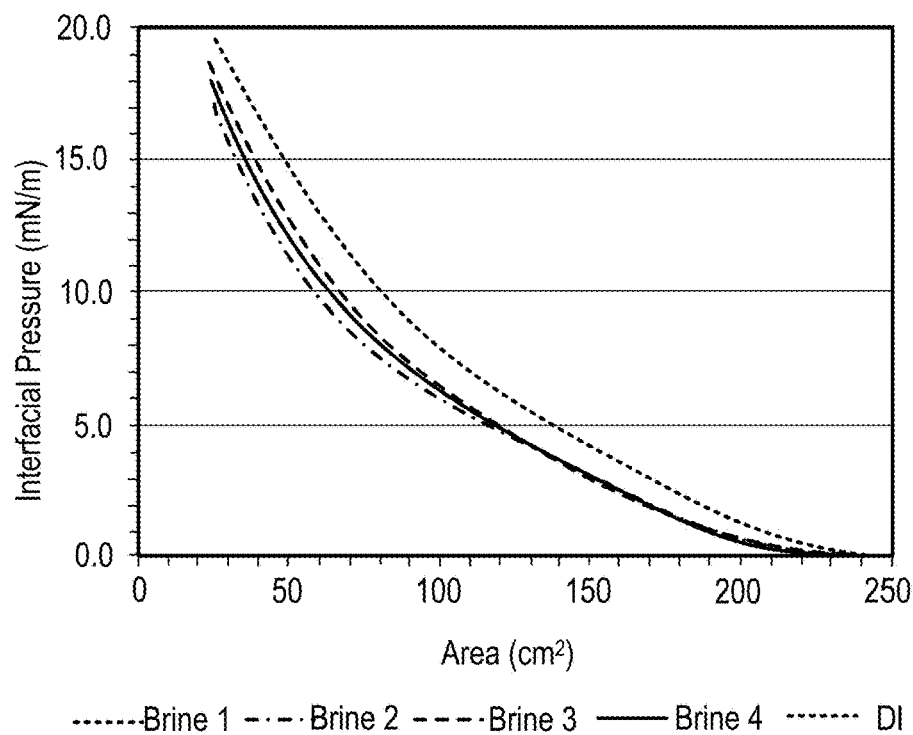
FIG. 4 shows interfacial pressure versus area for diluted crude oil-water interfaces from a Langmuir trough with various brines and deionized (DI) water

As illustrated in FIG. 4, the interfacial pressure increased with the compressing of the surface area for all the brines and DI water. The interfacial pressures are the greatest for DI water followed by Brine 4. On the other hand, the interfacial films containing Brines 1 and 2 showed the smallest interfacial pressures upon compression.

Since the compressional viscoelastic moduli are proportional to the ratio between the changes in the interfacial pressure and in the compressed area, the slope of the interfacial pressure-area isotherms is a good indication of the rigidity of the interfacial layer, with the steeper isotherms representing more rigid oil-aqueous phase interfacial layers. Therefore, the oil-DI water interfacial layer with the steepest isotherm is the most rigid, as compared with Brines 1-4.

Figure 5:
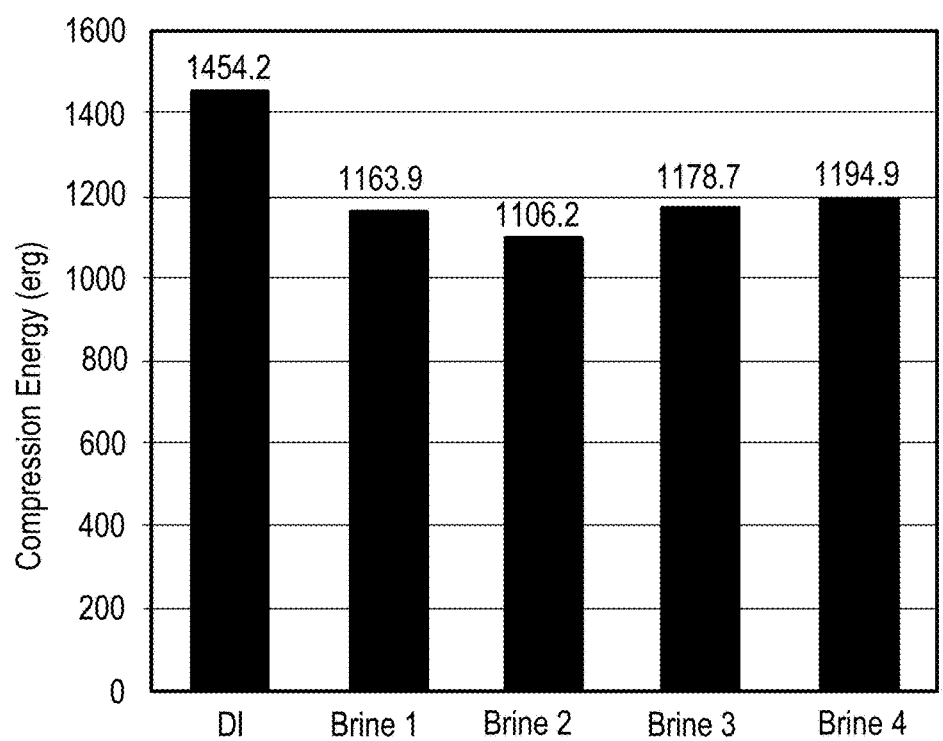
FIG. 5 shows compression energies for diluted crude oil-water interfacial films with various brines and DI water.

The compression energy, calculated by the integration of the interfacial pressure from FIG. 4 over the surface area change, quantified the difficulties to compress the interface. The computed compression energies (in erg, which is equal to $10^{-7}$ joules) for the crude oil-water interfacial films with Brines 1-4 are summarized in FIG. 5. It is evident from the results in FIG. 5 that it would take the largest energy to compress the crude oil-DI water interface. The interface became less rigid after the DI water was replaced by Brines 1-4. Among Brines 1-4, Brine 4 showed relatively larger compression energy and the smallest compression energy is demonstrated by Brine 2 followed by Brine 1. Having less interfacial film rigidity under compression is is more conducive of droplet coalescence. It is therefore anticipated that the presence of certain ions in the seawater and modified seawater such as calcium and magnesium speed up the coalescence of the crude oil droplets. In contrast, sulfate ions are expected to to delay the coalescence between oil droplets by contributing to the interfacial film rigidity.

Shear Rheology.

Figure 6A:
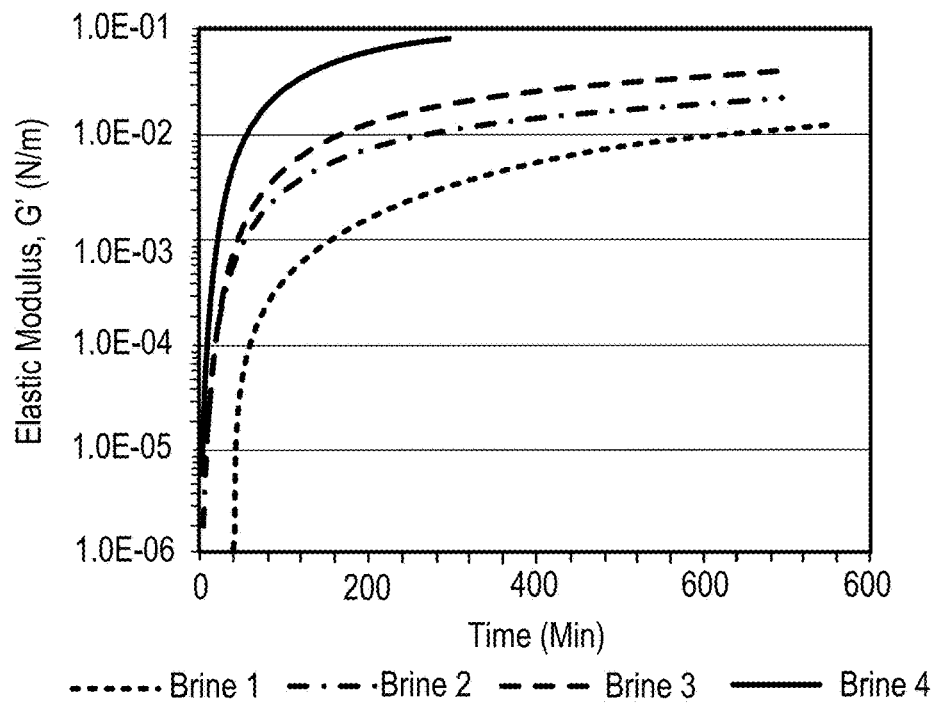
FIGS. 6A and 6B show elastic moduli and viscous moduli, respectively, versus time for crude oil-water interfacial films with various brines.
Figure 6B:
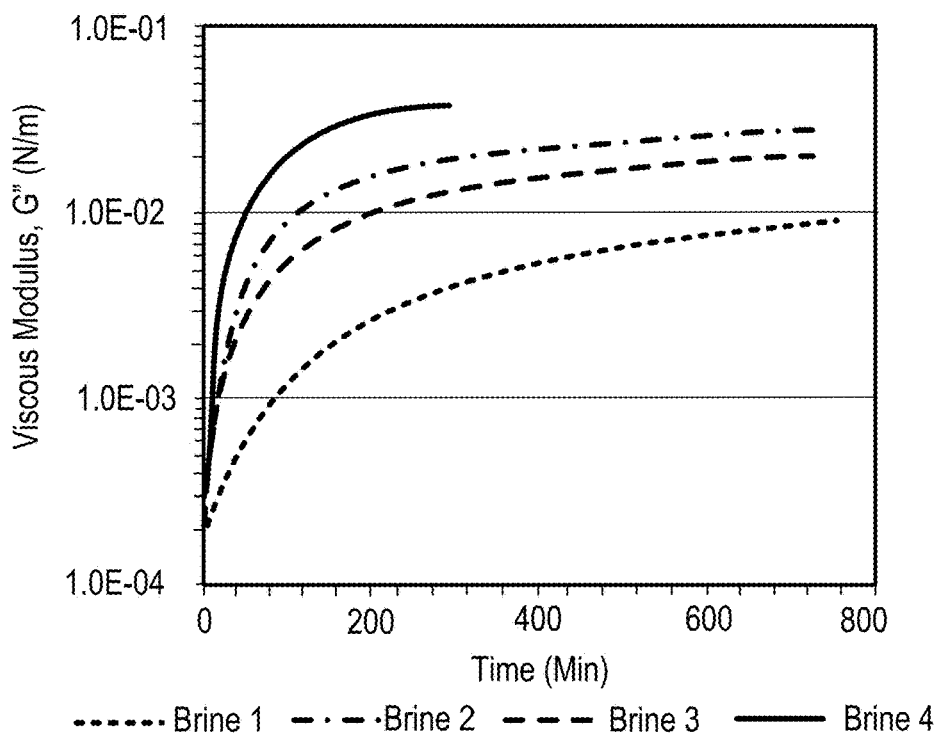

The elastic and viscous moduli are represented by the terms G' and G", respectively. The measured elastic moduli and viscous moduli for the crude oil-water interfacial films of Brines 1-4 are shown in FIGS. 6A and 6B, respectively.

Almost similar trends can be seen in both elastic and viscous moduli. Both viscous and elastic moduli were found to be greatest with Brine 4 followed by Brine 2, Brine 3, and Brine 1.

Figure 7:
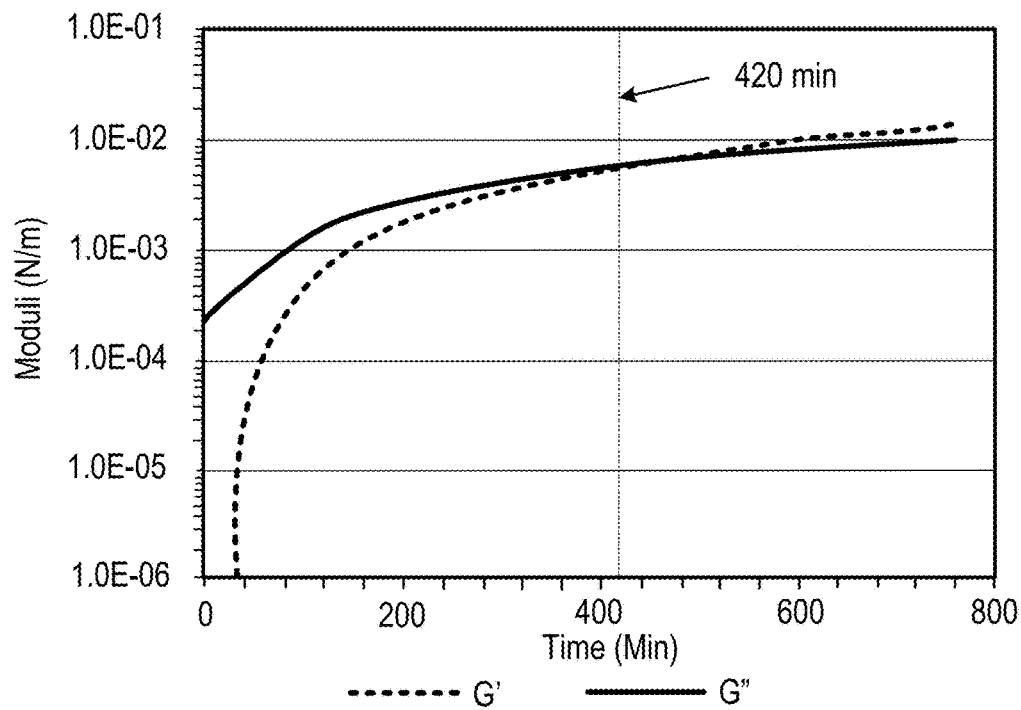
FIGS. 7-10 show elastic moduli and viscous moduli versus time for crude oil-water interfacial films with various brines.
Figure 8:
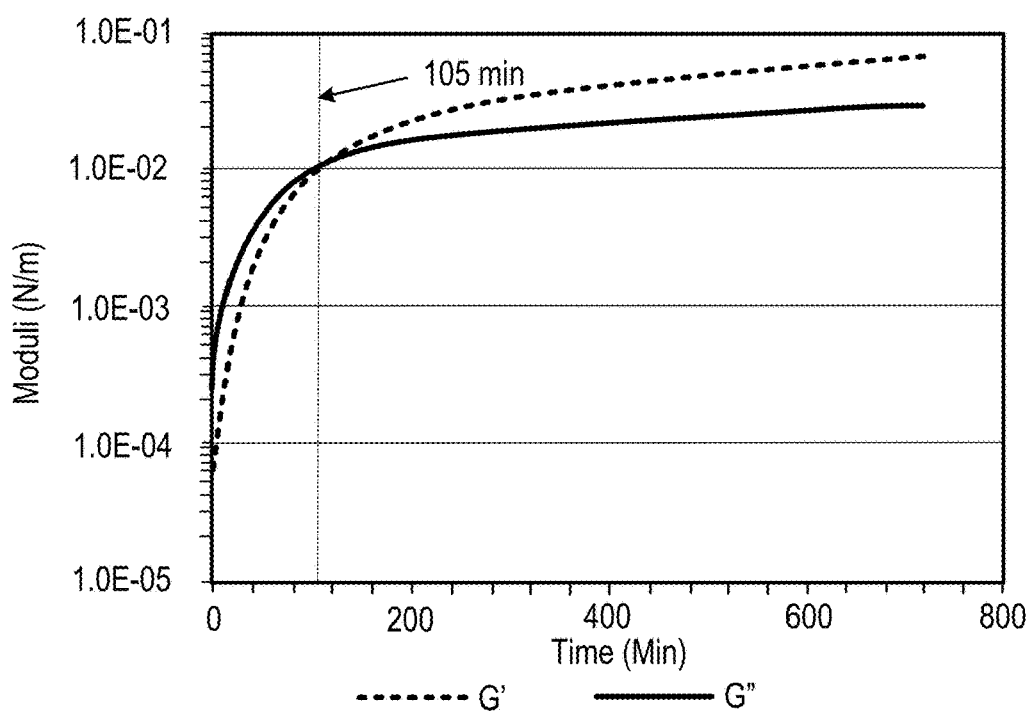
Figure 9:
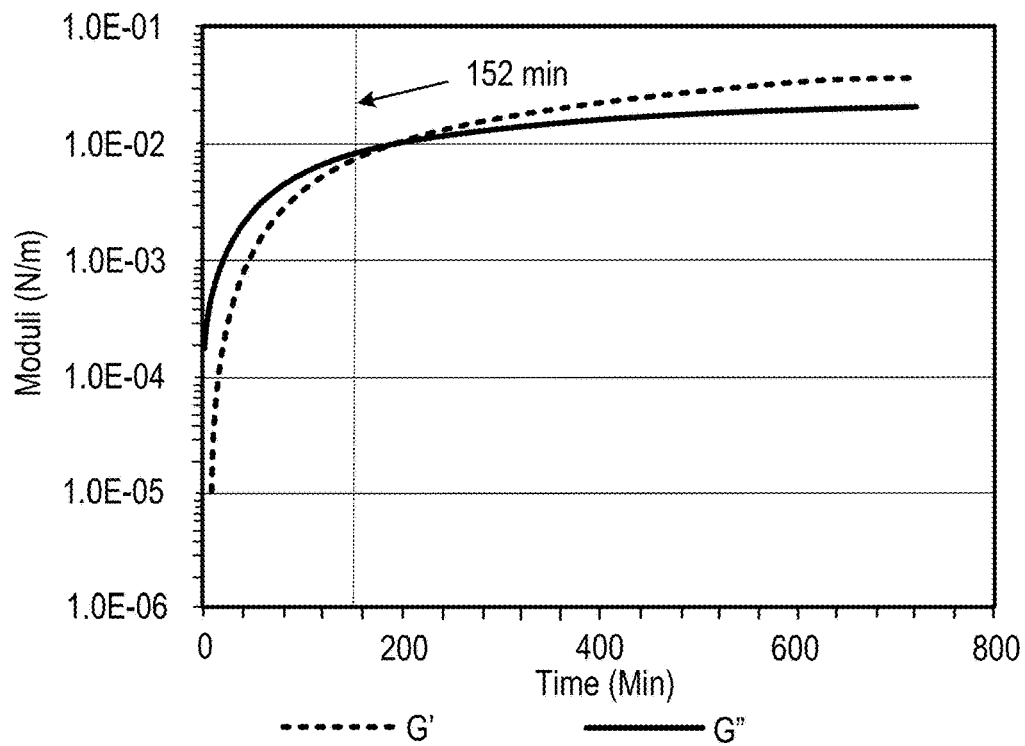
Figure 10:
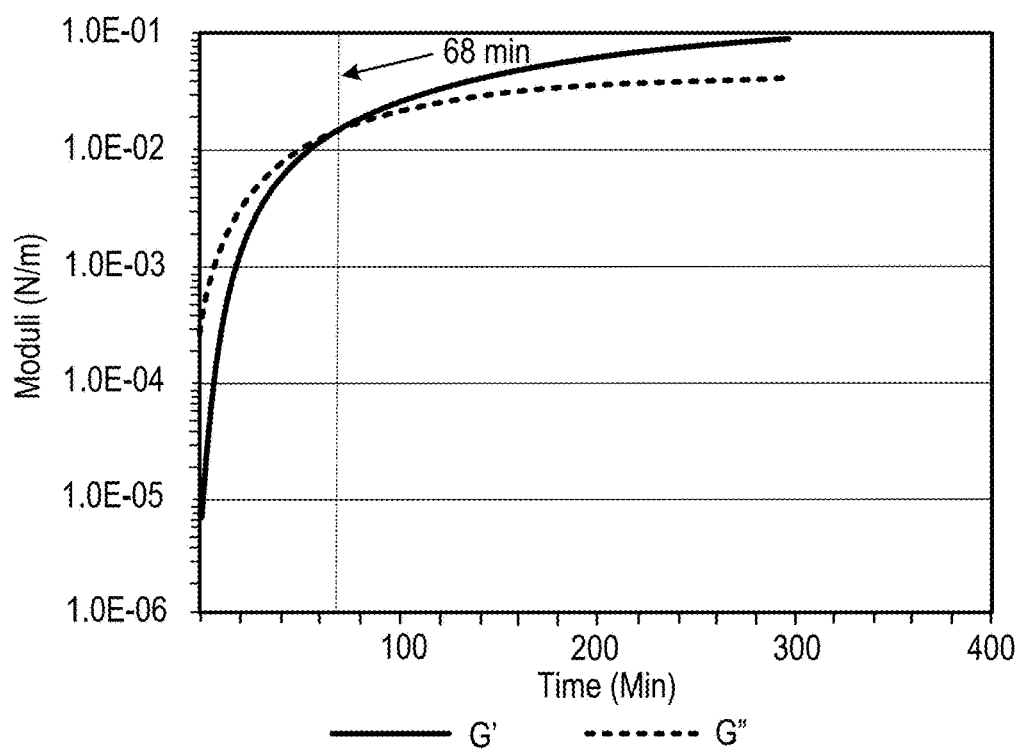
Figure 11:
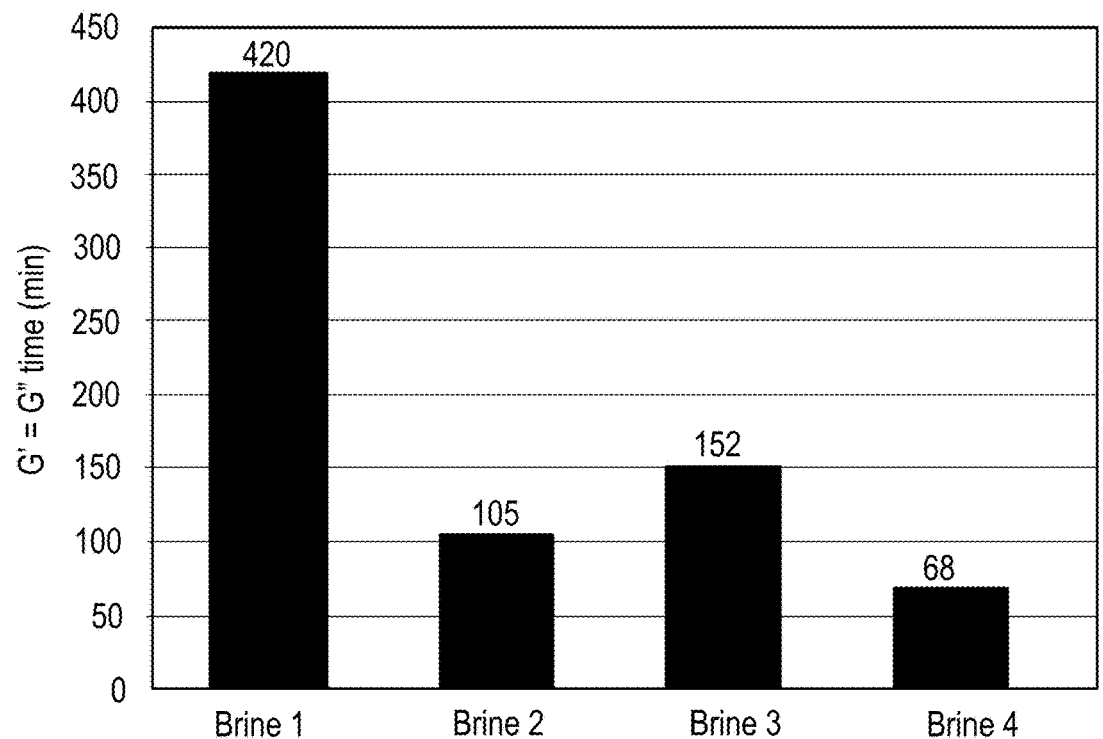
FIG. 11 shows times at which the elastic modulus and viscous modulus are equal for crude oil-water interfacial films with various brines.

The measured viscous and elastic moduli data are summarized in FIGS. 7-10 for Brines 1-4. As shown in these figures, the interfacial layers are viscous-dominant in the beginning and become elastic-dominant eventually for all these brines. However, the aging time for this transition to occur (that is, the time it takes for G'=G") is affected by the composition of the brine, as shown in FIGS. 7-10. The time it takes to reach G'=G" is also referred here as G'=G" time. A longer G'=G" time is an indication of a less rigid film. The interfacial layer of crude oil-Brine 1 was viscous dominant at the beginning (G">G') and become elastic-dominant (G'>G") after 420 min aging of the interface (FIG. 7). Similarly, the interfacial layer transitions from viscous-dominant (liquid-like) to elastic-dominant (solid-like) microstructures were detected after 105, 152, and 68 min aging for Brines 2, 3, and 4, respectively (FIGS. 8-10). The G'=G" times for different brines are summarized in FIG. 11, and as can be seen, the G'=G" time is in the order of Brine 1>Brine 3>Brine 2>Brine 4. The crude oil-Brine 1 interface therefore remained viscous-dominant for at least 420 min, which is beneficial to the coalescence of crude oil droplets because the elastic-dominant interface is hard to rupture. The quicker transition to elastic-dominant regime observed with Brine 4 when compared to other brines indicates the adverse impact of sulfate ions to result in stable rigid films and hinder the coalescence between oil droplets.

Figure 12:
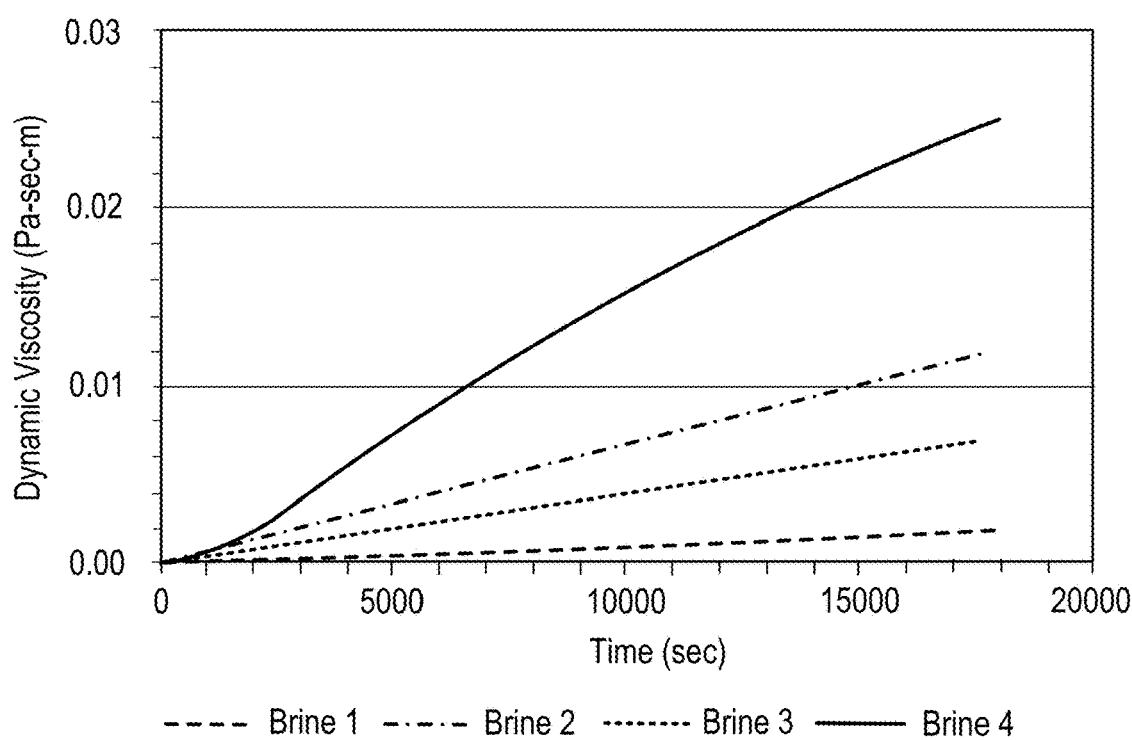
FIG. 12 shows dynamic viscosities for interfacial layers of various brines and crude oil.

The dynamic viscosities of the crude oil-water interfacial film obtained with different brines are shown in FIG. 12. These complex dynamic viscosities are computed from measured viscous and elastic moduli data using the Trios software connected to the rheometer based on similar methodology and equations described in Malkin et al., A.I. 2012. *Rheology: Concepts, Methods, and Applications*. Chapter 2 on Viscoelasticity, ChemTec Publishing, pp. 43-126. The dynamic viscosities of the interface were found to be larger for Brine 4 than for Brines 1-3. The dynamic interface viscosities are the least for Brine 1 and the greatest for Brine 4, with Brines 2 and 3 having intermediate values. The large interface viscosities observed with Brine 4 confirms the rigidity of the interfacial film. These rigid films are more stable and provide a mechanical barrier to retard the coalescence of released oil droplets and delay the formation of an oil bank.

Crumpling Ratio.

The crumpling behavior linked to the rigidity of the oil droplet-brine interface was shown by determining the wrinkles when the diluted crude oil droplet was contracted after aging in Brines 1-4. To quantify the extent of the crumpling, the crumpling ratio is defined as follows:

$$\text{Crumpling Ratio} = A_f/A_i \qquad \text{Eq. (2)},$$

where $A_i$ is the projected area of the initial oil droplet, and $A_f$ is the projected area of the oil droplet right before it crumples. Therefore, a larger crumpling ratio indicates a more rigid film because the droplet starts to crumple earlier. The images of the diluted crude oil drop obtained at the starting point of the contraction (top row) and at the starting point of crumpling (bottom row) with Brines 1-4 and DI water (left to right, respectively) are depicted for comparison in FIG. 13.

Figure 13:
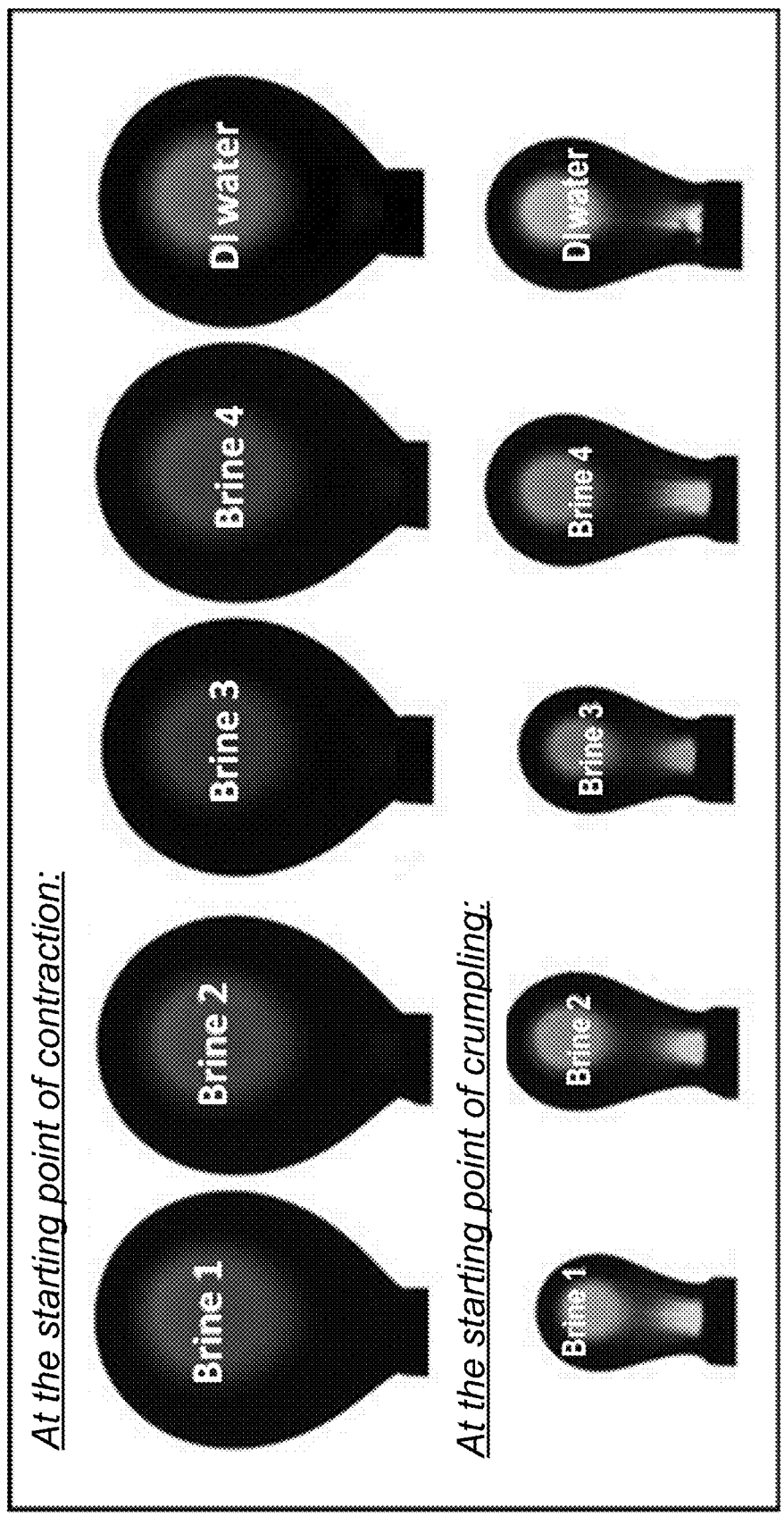
FIG. 13 shows crude oil droplet size in various brines and DI water.
Figure 14:
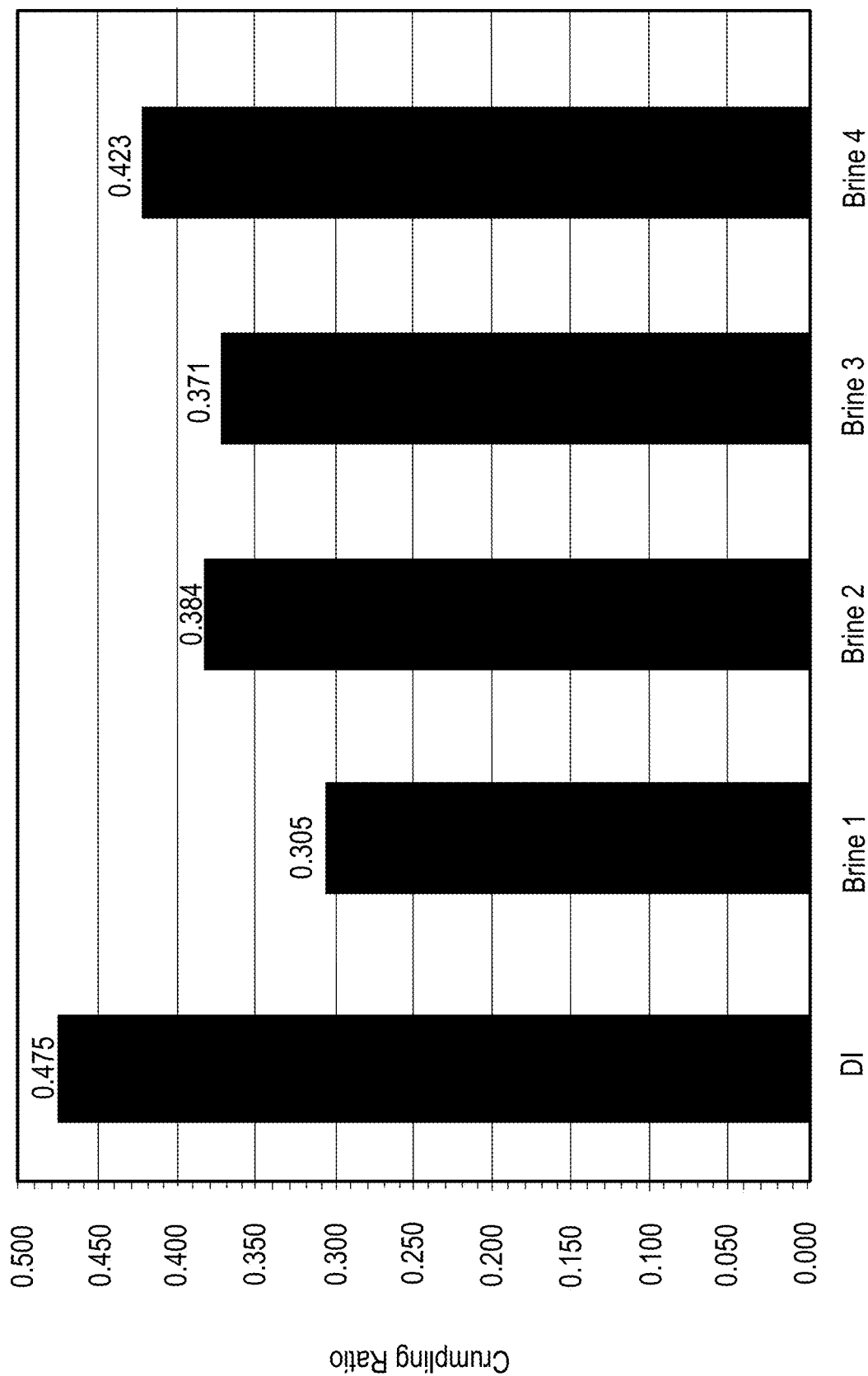
FIG. 14 shows a calculated crumpling ratio for DI water and various brines.
Figure 15A:
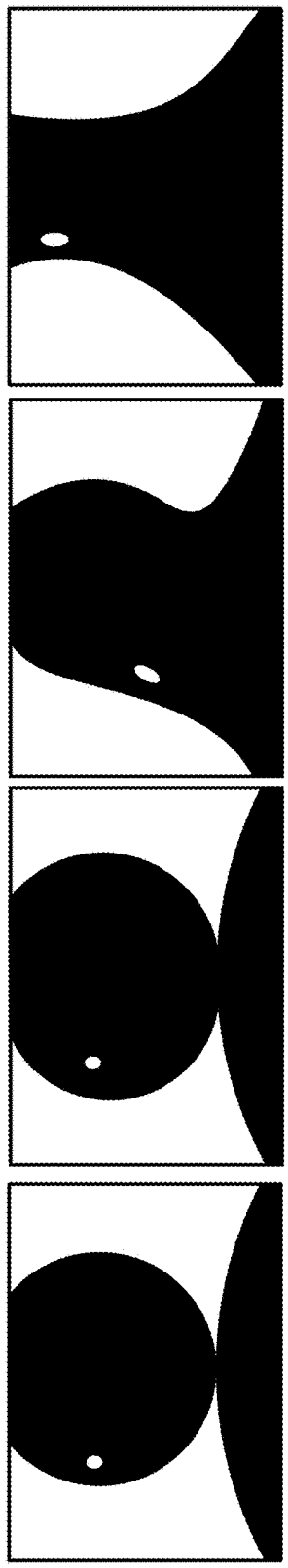
Figure 15B:
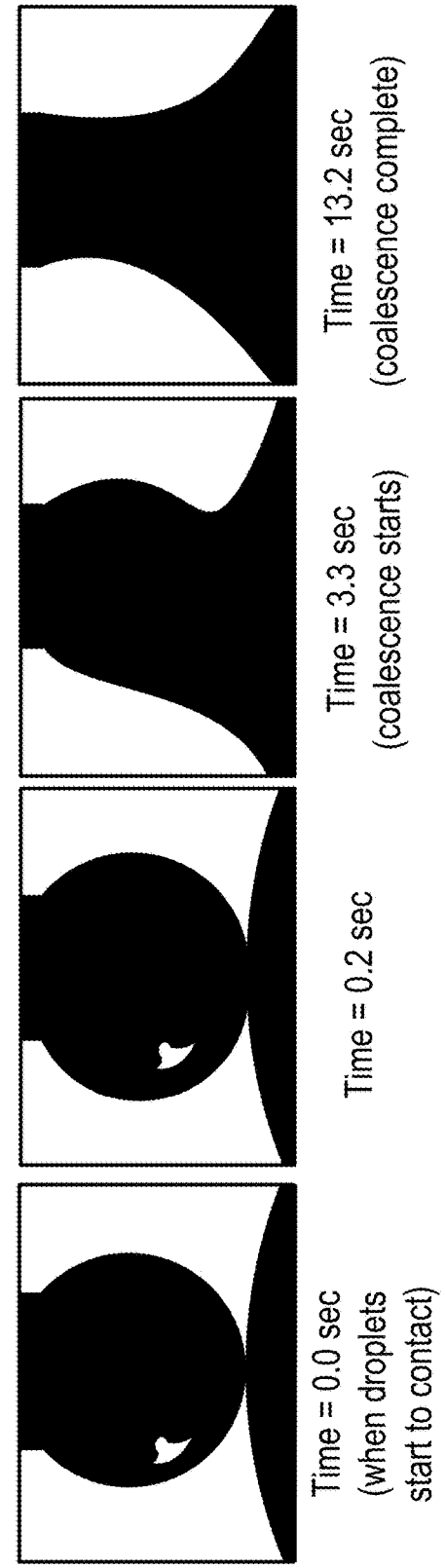
Figure 15E:
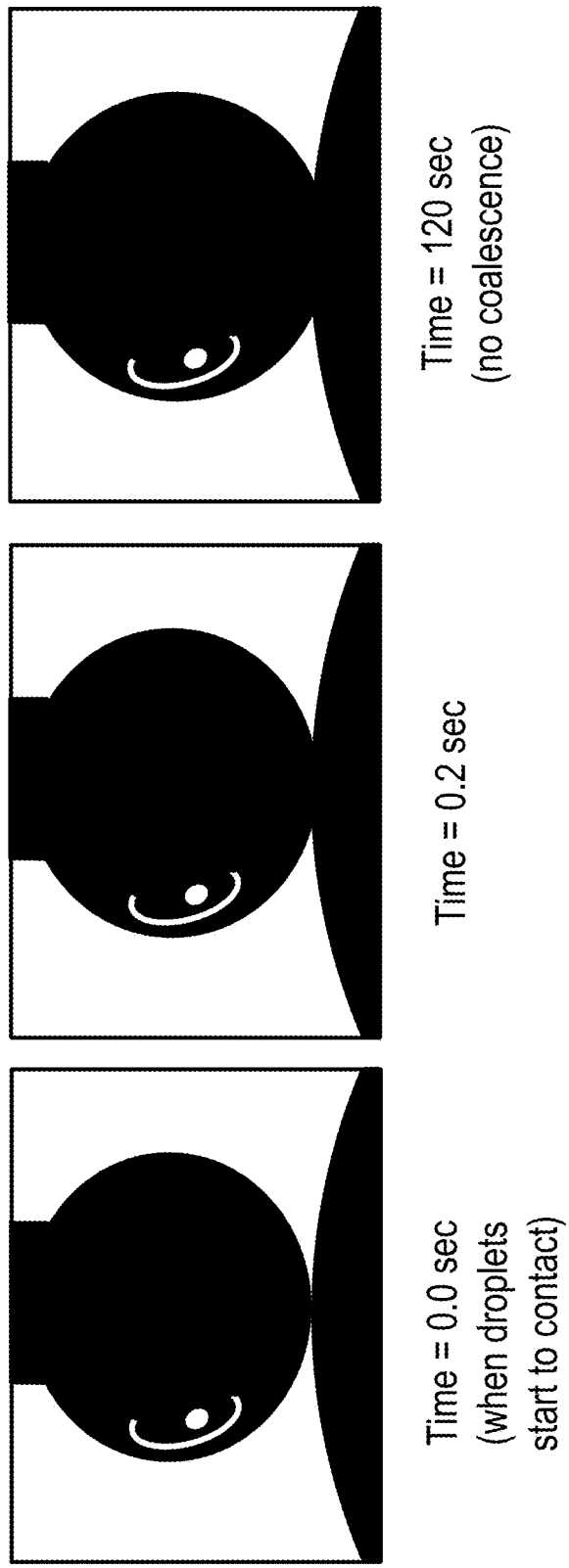

As depicted in FIG. 13, the surface of the droplets are smooth prior to contraction, while wrinkles are visible when the droplets begin to crumple. In view of the fact that the volume of the droplets was kept constant at 30 μL before contraction, the larger size of the crude oil droplet in DI water and sulfates-only brine (brine 4) at the point of crumpling indicates that the crumpling ratio in these waters is larger than in other brines. This finding is further confirmed by calculating the crumpling ratio. The crumpling ratio results are summarized in FIG. 14. As expected, the smallest crumpling ratio is observed for the droplet in Brine 1. The interface of crude oil-Brine 1 is therefore the softest. On the other hand, DI water and Brine 4 showed greater crumpling ratios, indicating the hard rigid films due to formation of skin at the interface. Brines 2 and 3 showed almost similar crumpling behavior. These crumpling ratio results therefore agree well with other results from Langmuir trough and shear rheology experiments to confirm the adverse impact of DI water and sulfates-only brine on interfacial film stability to retard the coalescence between oil droplets.

Coalescence Time.

By accurately controlling the size and the alignment of two droplets, the coalescence time measurement is found to be reproducible with different brines. At the beginning, a larger difference of the coalescence time in fresh DI water was observed in different trials due to the presence of tiny air bubbles in the water. During the aging period of the droplets prior to the coalescence time measurement, those tiny air bubbles coalesced with the bottom droplet to accelerate the coalescence of the bottom droplet with the top droplet. To avoid this artifact in the experiments, the DI water was first stored at room temperature for a period of time prior to being pipetted into the steel container. The precipitation of the air bubbles onto the Teflon holder is anticipated to decrease with increasing storage (equilibration) time. No coalescence was observed up to 120 seconds (upper limit of the video recording) with DI water after 7-hours or 24-hours of storage. As a result, the coalescence time of DI water was assumed to be greater than 120 seconds. Snapshots captured from the video frames on dynamic coalescence behavior of crude oil droplets in Brines 1-4 and DI water are shown in FIGS. 15A-15E, respectively. The time required to start coalescence of oil droplets from their initial contact is determined to be the actual coalescence time from these video frames.

Figure 16:
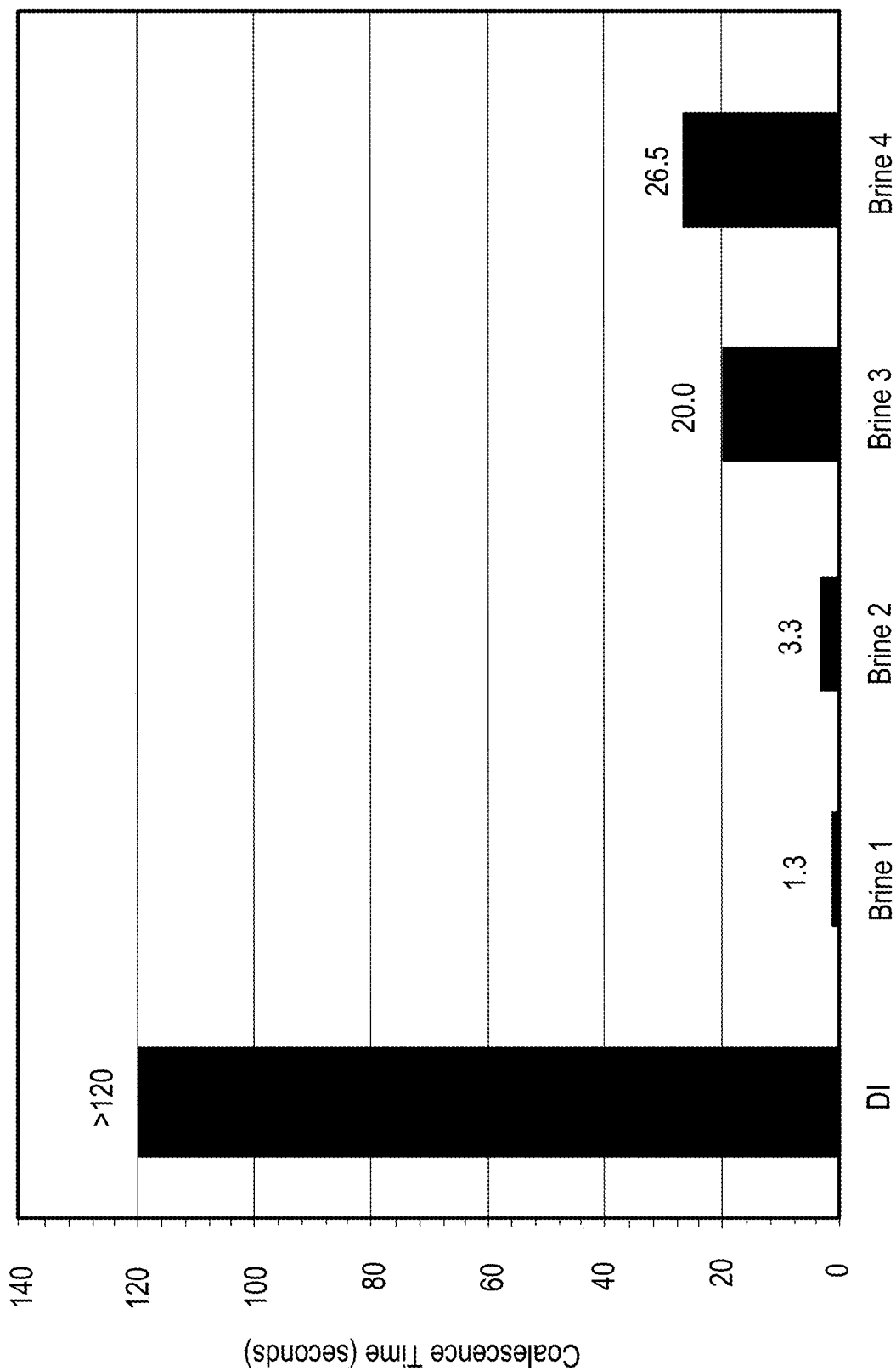
FIG. 16 shows coalescence time of oil droplets in various brines and DI water.

The results of oil droplet coalescence times obtained with Brines 1-4 and DI water are summarized in FIG. 16. As shown in FIG. 16, the coalescence of crude oil droplets is the fastest in Brine 1, followed by Brine 2, Brine 3, Brine 4, and DI water. DI water showed the longest coalescence time whereas Brine 4 showed the delayed coalescence of crude oil droplets when compared to Brines 1-3. These results therefore showed a consistent trend in agreement with large interfacial film compression energies, short G'=G" transition times, large dynamic interface viscosities, and large crude oil droplet crumpling ratios observed in both DI water and Brine 4.

Film rigidity, as quantified by the compression energy of the interfacial layer (Langmuir trough), G'=G" time (shear rheology), dynamic interface viscosities (shear rheology), and crumpling ratio demonstrated consistency among these several microscopic scale parameters, and the coalescence time data for crude oil droplets obtained in Brines 1-4 and DI water were shown to correlate with the rigidity of interfacial film as quantified from different interfacial measurement techniques.

The enhanced oil droplet coalescence obtained with Brines 1 and 2 can be attributed to both salinity and the presence of certain ions such as calcium and magnesium.

The major function of salts and these ions in brines is to soften the oil-water interface so that the interfacial layers can be easily deformed and broken down to facilitate the coalescence. The favorable effects of these divalent cations seem to outweigh the negative contributions from sulfate ions on the interfacial film rigidity. On the other hand, it becomes hard to coalesce oil droplets in the presence of DI water. Interestingly, the oil droplet coalescence is improved in Brines 3 and 4 compared to DI water. However delayed oil droplet coalescence was observed with Brine 4 compared to Brine 3.

Results are summarized below.

1) The interfacial pressure vs. molecular area isotherms from the Langmuir trough experiments showed the increase of interfacial pressure with the compression of the surface area for Brines 1-4 and DI water. The interfacial pressures are the largest for DI water followed by Brine 4. Larger interface compression energies obtained with DI water and Brine 4, when compared to Brines 1-3, indicate the rigidity of the interfacial film to hinder the coalescence between oil droplets.

2) The viscous and elastic moduli are found to be largest with Brine 4. The interfacial layers are viscous-dominant at the beginning and eventually become elastic-dominant for Brines 1-4. The transition times required for the interfacial film to become elastic-dominant from viscous-dominant microstructures is shorter for Brine 4 than Brines 1-3. These quicker transitions to elastic-dominant regime indicate the detrimental effect of sulfate ions to form stable rigid films at the interface. The dynamic interface viscosities were also found to be larger for Brine 4, which once again confirms the formation of rigid interfacial film.

3) Both DI water and Brine 4 showed larger crude oil droplet crumpling ratios, which indicated the presence of hard films due to rigid skin at the interface. These crumpling ratio results agreed well with Langmuir trough and shear rheology data to confirm the adverse impact of DI water and Brine 4 on the interfacial film stability and oil droplet coalescence.

4) DI water showed the longest coalescence time for crude oil droplets, whereas Brine 4 displayed delayed coalescence compared to other Brines 1-3. These results showed a consistent trend in agreement with larger interfacial compression energies, shorter transition times to the elastic regime, larger dynamic interface viscosities, and larger crude oil crumpling ratios observed in Brine 4 and DI water.

5) The interfacial film rigidity was successfully quantified in this study by the compression energy of the interfacial layer (Langmuir trough), G'=G" time (shear rheology), dynamic interface viscosity (shear rheology), and crumpling ratio. The coalescence times for crude oil droplets obtained in Brines 1-4 and DI water were shown to correlate well with interfacial film rigidity as quantified from different interfacial measurement techniques.

6) DI water was shown to be unfavorable for use in a Smart water flood, given the unfavorable fluid-fluid interactions observed at the interface. Adequate salinity and a sufficient amount of calcium and magnesium ions in the Smart water are desired to result in favorable microscopic scale interactions at the crude oil-water interface to promote coalescence between released oil droplets and form the oil bank. Such water recipes are expected to increase oil phase connectivity, hasten oil recovery from a Smart water flood with reduced water cut in the production.

Based on these results, water recipes may be tuned for faster oil recovery in a Smart water flood by establishing favorable water ion interactions at fluid-fluid interfaces without substantially compromising ultimate recovery, which is governed at least in part by the interactions at rock-fluid interface.

Thus, particular implementations of the subject matter have been described. Other implementations are within the scope of the claims.

What is claimed is:

1. A method of assessing a rigidity of an interface between a crude oil and a brine, the method comprising at least one of:
    assessing a compression energy for the interface between the crude oil and the brine;
    assessing a time at which an elastic modulus and a viscous modulus of the interface between the crude oil and the brine are equal;
    assessing a crumpling behavior or a crumpling ratio of a droplet of the crude oil, wherein the droplet of the crude oil is in the brine; and
    assessing a coalescence time of a plurality of droplets of the crude oil, wherein the plurality of droplets of the crude oil is in the brine.

2. The method of claim 1, wherein assessing a compression energy for the interface between the crude oil and the brine comprises:
    assessing interfacial pressure versus area isotherms for the interface between the crude oil and the brine; and
    integrating the interfacial pressure over a change in surface area to yield the compression energy.

3. The method of claim 2, wherein assessing interfacial pressure versus area isotherms for the interface between the crude oil and the brine is achieved with a Langmuir trough.

4. The method of claim 1, wherein assessing a time at which an elastic modulus and a viscous modulus of the interface between the crude oil and the brine are equal comprises:
    assessing elastic moduli and viscous moduli of the interface between the crude oil and the brine as a function of time; and
    identifying a time at which the elastic modulus is equal to the viscous modulus.

5. The method of claim 4, further comprising assessing a dynamic interfacial viscosity using the elastic moduli and the viscous moduli.

6. The method of claim 4, wherein assessing elastic moduli and viscous moduli of the interface between the crude oil and the brine as a function of time is achieved with an interfacial shear rheometer.

7. The method of claim 1, wherein assessing the crumpling ratio of the droplet of the crude oil comprises:
    assessing an initial size of the droplet of the crude oil before initiating a contraction of the droplet of the crude oil; and
    assessing a size of the droplet of the crude oil at the time at which crumpling begins.

8. The method of claim 1, wherein the crumpling ratio is a projected area of the droplet of the crude oil just before the droplet of the crude oil crumples divided by an initial projected area of the droplet of the crude oil.

9. The method of claim 1, wherein the brine comprises ions of at least one of sodium, calcium, magnesium, chloride, bicarbonate, and sulfate.

10. The method of claim 1, wherein the brine is substantially free of sulfate.

11. The method of claim 1, wherein assessing the rigidity of the interface between the crude oil and the brine comprises assessing the compression energy for the interface between the crude oil and the brine, and further comprising selecting a composition of an injection fluid for a reservoir from which the crude oil was obtained by increasing or decreasing a concentration of at least one ion in the brine to decrease the rigidity of the interface between the crude oil and the brine.

12. The method of claim 1, wherein assessing the rigidity of the interface between the crude oil and the brine comprises assessing the time at which the elastic modulus and the viscous modulus of the interface between the crude oil and the brine are equal, and further comprising selecting a composition of an injection fluid for a reservoir from which the crude oil was obtained by increasing or decreasing a concentration of at least one ion in the brine to decrease the rigidity of the interface between the crude oil and the brine.

13. The method of claim 1, wherein assessing the rigidity of the interface between the crude oil and the brine comprises assessing the crumpling behavior or the crumpling ratio of the droplet of the crude oil in the brine, and further comprising selecting a composition of an injection fluid for a reservoir from which the crude oil was obtained by increasing or decreasing a concentration of at least one ion in the brine to decrease the rigidity of the interface between the crude oil and the brine.

14. The method of claim 1, wherein assessing the rigidity of the interface between the crude oil and the brine comprises assessing a coalescence time of droplets of the crude oil in the brine, and further comprising selecting a composition of an injection fluid for a reservoir from which the crude oil was obtained by increasing or decreasing a concentration of at least one ion in the brine to decrease the rigidity of the interface between the crude oil and the brine.

15. The method of claim 1, further comprising:
obtaining a sample of the crude oil from a reservoir before assessing the rigidity of the interface between the crude oil and the brine;
selecting a composition of an injection fluid for the reservoir from which the crude oil was obtained by increasing or decreasing a concentration of at least one ion in the brine to decrease the rigidity of the interface between the crude oil and the brine; and
injecting the injection fluid into the reservoir.

16. A method of selecting a composition of an injection fluid for an enhanced oil recovery process, the method comprising:
assessing a rigidity of an interface between a crude oil and a brine; and
selecting the composition of the injection fluid, wherein selecting the composition of the injection fluid comprises altering a composition of the brine to increase or decrease a concentration of one or more ions in the brine to yield the injection fluid, such that a crude oil-injection fluid interfacial film rigidity is less than a crude oil-brine interfacial film rigidity.

17. The method of claim 16, wherein assessing the rigidity of the interface between the crude oil and the brine comprises at least one of:
assessing a compression energy for the interface between the crude oil and the brine;
assessing a time at which an elastic modulus and a viscous modulus of the interface between the crude oil and the brine are equal;
assessing a crumpling behavior or a crumpling ratio of a droplet of the crude oil, wherein the droplet of the crude oil is in the brine; and
assessing a coalescence time of a plurality of droplets of the crude oil, wherein the plurality of droplets of the crude oil is in the brine.

18. The method of claim 16, further comprising obtaining a sample of the crude oil from a reservoir before assessing the rigidity of the interface between the crude oil and the brine.

19. The method of claim 18, further comprising injecting the injection fluid into the reservoir.

20. The method of claim 16, comprising increasing a concentration of at least one of sodium ions, calcium ions, magnesium ions, chloride ions, bicarbonate ions, or sulfate ions in the brine to decrease the rigidity of the interface between the crude oil and the brine.

21. The method of claim 16, comprising decreasing a concentration of sulfate ions in the brine to decrease the rigidity of the interface between the crude oil and the brine.

* * * * *